(12) United States Patent  
Koma

(10) Patent No.: US 10,065,902 B2  
(45) Date of Patent: Sep. 4, 2018

(54) BUTADIENE PRODUCTION SYSTEM AND BUTADIENE PRODUCTION METHOD

(71) Applicant: SEKISUI CHEMICAL CO., LTD., Osaka (JP)

(72) Inventor: Satoshi Koma, Tokyo (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 0 days.

(21) Appl. No.: 15/531,120

(22) PCT Filed: Jan. 13, 2016

(86) PCT No.: PCT/JP2016/050820  
§ 371 (c)(1),  
(2) Date: May 26, 2017

(87) PCT Pub. No.: WO2016/114299  
PCT Pub. Date: Jul. 21, 2016

(65) Prior Publication Data

US 2017/0334805 A1    Nov. 23, 2017

(30) Foreign Application Priority Data

Jan. 13, 2015    (JP) .................................. 2015-004461

(51) Int. Cl.
*C07C 1/20* (2006.01)  
*C10K 3/00* (2006.01)  
(Continued)

(52) U.S. Cl.  
CPC .............. *C07C 1/20* (2013.01); *C07C 29/151* (2013.01); *C10J 3/72* (2013.01); *C10K 3/00* (2013.01); *C10J 2300/0946* (2013.01)

(58) Field of Classification Search  
CPC ..... B01J 23/6562; B01J 23/80; C07C 1/2076; C07C 2521/08; C07C 2523/80; C07C 29/151; C07C 29/36; C07C 45/49  
See application file for complete search history.

(56) References Cited

U.S. PATENT DOCUMENTS

2012/0071697 A1    3/2012    Ichikawa  
2013/0210096 A1    8/2013    Schultz et al.

FOREIGN PATENT DOCUMENTS

CN    102424359    5/2013  
JP    2011-57869    3/2011  
(Continued)

OTHER PUBLICATIONS

International Search Report dated Mar. 8, 2016 in International (PCT) Application No. PCT/JP2016/050820.  
(Continued)

*Primary Examiner* — Sharon Pregler  
(74) *Attorney, Agent, or Firm* — Wenderoth, Lind & Ponack, L.L.P.

(57) ABSTRACT

A butadiene production system and a butadiene production method are provided in which the yield is high and environmental load can be reduced. The butadiene production system (1) includes: a gas preparation device (10) that heats raw materials to prepare a mixed gas including hydrogen and carbon monoxide; an ethanol production device (12) that is provided downstream of the gas preparation device (10) and brings the mixed gas into contact with a first catalyst to obtain ethanol; a butadiene production device (16) that is provided downstream of the ethanol production device (12) and brings the ethanol into contact with a second catalyst to obtain butadiene; and return means (18) for returning hydrogen, ethylene, and the like, which are produced as by-products in the butadiene production device (Continued)

(16), to the gas preparation device (10). In addition, in the butadiene production method, the butadiene production system (1) is used.

18 Claims, 2 Drawing Sheets

(51) Int. Cl.
    *C10J 3/72*    (2006.01)
    *C07C 29/151*  (2006.01)

(56) References Cited

FOREIGN PATENT DOCUMENTS

| | | |
|---|---|---|
| JP | 2012-1441 | 1/2012 |
| JP | 2013-121939 | 6/2013 |
| JP | 2013-199461 | 10/2013 |
| WO | 2010/092819 | 8/2010 |
| WO | 2012/058508 | 5/2012 |
| WO | 2012/087949 | 6/2012 |
| WO | 2013/081779 | 6/2013 |
| WO | 2013/125389 | 8/2013 |
| WO | 2014/031246 | 2/2014 |
| WO | 2014/049158 | 4/2014 |

OTHER PUBLICATIONS

Extended European Search Report dated Jun. 1, 2018 in European Application No. 16737370.3.

BUTADIENE PRODUCTION SYSTEM AND BUTADIENE PRODUCTION METHOD

TECHNICAL FIELD

The present invention relates to a butadiene production system and a butadiene production method.

Priority is claimed on Japanese Patent Application No. 2015-4461, filed on Jan. 13, 2015, the content of which is incorporated herein by reference.

BACKGROUND ART

Butadiene such as 1,3-butadiene is used as a raw material of styrene-butadiene rubber (SBR) or the like. In general, butadiene is purified from a C4 fraction which is produced as a by-product when ethylene is synthesized from petroleum.

However, recently, bioethanol synthesized from a biomass-derived raw material has attracted attention as an alternative raw material to petroleum. For example, PTL 1 discloses a method of producing butadiene from ethanol using a catalyst.

However, in the method of obtaining butadiene from ethanol using the catalyst as in PTL 1, the yield is not industrially sufficiently high. In addition, when butadiene is industrially produced, it is important to reduce a load on the global environment as much as possible.

CITATION LIST

Patent Literature

[PTL 1] PCT International Publication No. WO2013/125389

SUMMARY OF INVENTION

Technical Problem

An object of the present invention is to provide a butadiene production system and a butadiene production method in which the yield is high and environmental load can be reduced.

Solution to Problem

A butadiene production system (apparatus) according to the present invention includes: a gas preparation device that heats raw materials to prepare a mixed gas including hydrogen and carbon monoxide; an ethanol production device that is provided downstream of the gas preparation device and brings the mixed gas into contact with a first catalyst to obtain ethanol; a butadiene production device that is provided downstream of the ethanol production device and brings the ethanol into contact with a second catalyst to obtain butadiene; and return means for returning at least a portion of the gas other than butadiene from the butadiene production device to the gas preparation device.

It is preferable that the return means include a pipe through which the butadiene production device and the gas preparation device are connected.

It is preferable that the gas preparation device include a gasification furnace and a reforming furnace, that the gasification furnace thermally decompose solid raw materials to produce the mixed gas including hydrogen and carbon monoxide, and that the reforming furnace be provided downstream of the gasification furnace and reform hydrocarbon in the mixed gas into hydrogen and carbon monoxide.

It is preferable that the return means be means for returning at least a portion of the gas other than butadiene to the reforming furnace.

A butadiene production method according to the present invention includes: a gas preparation step of heating raw materials to prepare a mixed gas including hydrogen and carbon monoxide; an ethanol production step of bringing the mixed gas into contact with a first catalyst to obtain ethanol; a butadiene production step of bringing the ethanol into contact with a second catalyst to obtain butadiene; and a return step of returning at least a portion of the gas other than butadiene from the butadiene production step to the gas preparation step.

It is preferable that the gas preparation step include a gasification operation and a reforming operation, that, in the gasification operation, solid raw materials be thermally decomposed to produce the mixed gas including hydrogen and carbon monoxide, and that, in the reforming operation, hydrocarbon in the mixed gas be reformed into hydrogen and carbon monoxide.

It is preferable that the return step be a step of returning at least a portion of the gas other than butadiene to the reforming operation.

Advantageous Effects of Invention

In the butadiene production system according to the present invention, the yield of butadiene is high, and environmental load can be reduced.

In the butadiene production method according to the present invention, butadiene can be produced with a high yield, and environmental load can be reduced.

DESCRIPTION OF EMBODIMENTS

The definitions of the following terms are applied to this specification and claims.

The meaning of "returning at least a portion of the gas other than butadiene to the gas preparation device" includes a configuration of returning at least a portion of the gas other than butadiene such that the temperature of the mixed gas emitted from the gas preparation device is held at a temperature (for example, 1000° C. to 1200° C.) at which carbon monoxide is synthesized from the returned gas due to an equilibrium reaction represented by $CO_2+H_2 \Leftrightarrow CO+H_2O$ or a reaction represented by $C_nH_m+nH2O \rightarrow nCO+(m/2+n)H_2$. For example, a configuration is included in which, in the pipe connected to the reforming furnace of the gas preparation device, hydrogen is returned to a portion where the temperature of the mixed gas is held at a temperature at which the equilibrium reaction is sufficiently shifted to the carbon monoxide side such that carbon dioxide in the pipe is converted into carbon monoxide. In addition, another configuration is included in which, in the pipe connected to the reforming furnace of the gas preparation device, ethylene is returned to a portion where carbon monoxide is synthesized from hydrocarbon in the mixed gas due to the reaction such that ethylene in the pipe is converted into carbon monoxide.

The meaning of "returning at least a portion of the gas other than butadiene to the gas preparation step" includes a configuration of returning at least a portion of the gas other than butadiene to a step where the temperature of the mixed gas heated in the gas preparation step is held at a temperature at which carbon monoxide is synthesized due to the equilibrium reaction or a reaction of synthesizing carbon monoxide from hydrocarbon. The same can be applied to the meaning of "returning at least a portion of the gas other than butadiene to the reforming operation".

"Raw materials" are organic materials from which the mixed gas including hydrogen and carbon monoxide is obtained by heating, and include both of solid raw materials such as biomass or organic waste and raw material gases such as natural gas or waste gas.

"CO conversion ratio" refers to a percentage of the number of moles of carbon monoxide consumed by a reaction to the number of moles of carbon monoxide in the mixed gas.

"Selection ratio" refers to a percentage of the number of moles of carbon monoxide converted into a specific compound to the number of moles of carbon monoxide consumed in the mixed gas.

First Embodiment (Butadiene Production System)

In a butadiene production system according to the present invention, raw materials are heated to prepare a mixed gas including hydrogen and carbon monoxide, ethanol is obtained from the mixed gas, and butadiene is produced from the ethanol. Hereinafter, an example of the butadiene production system according to the present invention will be described.

Figure 1:
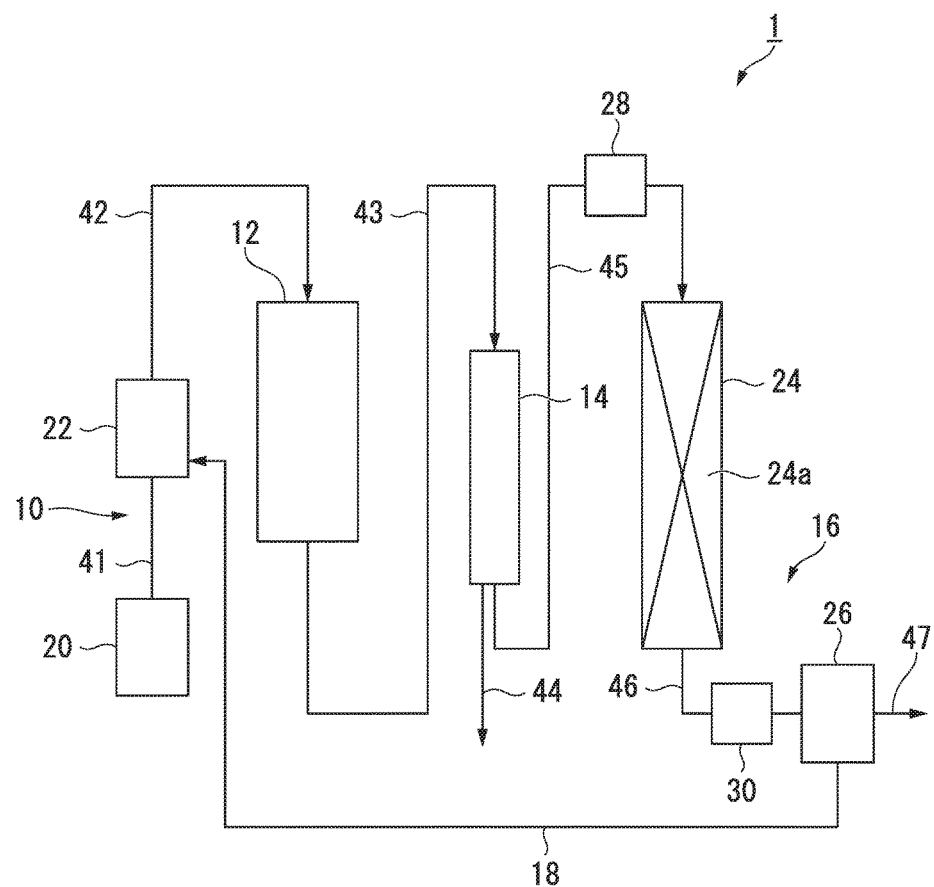
FIG. 1 is a schematic diagram showing an example of a butadiene production system according to the present invention.

As shown in FIG. 1, a butadiene production system 1 according to the embodiment includes: a gas preparation device 10; an ethanol production device 12 that is provided downstream of the gas preparation device 10; a purification device 14 that is provided downstream of the ethanol production device 12; a butadiene production device 16 that is provided downstream of the purification device 14; and return means 18 for returning at least a portion of the gas other than butadiene from the butadiene production device 16 to the gas preparation device 10. The gas preparation device 10 includes a gasification furnace 20 and a reforming furnace 22 that is provided downstream of the gasification furnace 20. The butadiene production device 16 includes a reaction pipe 24 and a gas-liquid separator 26 that is provided downstream of the reaction pipe 24.

The gasification furnace 20 and the reforming furnace 22 are connected to each other through a pipe 41. The reforming furnace 22 and the ethanol production device 12 are connected to each other through a pipe 42. The ethanol production device 12 and the purification device 14 are connected to each other through a pipe 43. An exhaust pipe 44 is connected to the purification device 14. The purification device 14 and the reaction pipe 24 of the butadiene production device 16 are connected to each other through a pipe 45. The reaction pipe 24 and the gas-liquid separator 26 are connected to each other through a pipe 46. A pipe 47 is connected to the gas-liquid separator 26.

In this example, the reforming furnace 22 of the gas preparation device 10 and the gas-liquid separator 26 of the butadiene production device 16 are connected to each other through a pipe included in the return means 18.

The gas preparation device 10 heats raw materials to prepare a mixed gas including hydrogen and carbon monoxide at an arbitrary ratio, and includes the gasification furnace 20 and the reforming furnace 22.

The gasification furnace 20 thermally decomposes solid raw materials such as biomass, organic waste (for example, waste plastic, waste paper, or waste cloth), or coal to produce a mixed gas including hydrogen and carbon monoxide. As the gasification furnace 20, for example, a furnace that can produce the mixed gas by firing a portion of biomass or organic waste in the presence of oxygen so as to be thermally oxidized can be adopted. As the gasification furnace, a fluidized bed type gasification furnace is preferable. The fluidized bed type gasification furnace is preferable from the viewpoint that it is not likely to be affected by the forms of the raw materials and the viewpoint that the amount of auxiliary fuel used is small.

The reforming furnace 22 hydrocarbon in the mixed gas reacts with water so as be reformed into hydrogen and carbon monoxide. In the reforming furnace 22, the concentration of carbon monoxide in the mixed gas produced from the gasification furnace 20 is increased such that a ratio between hydrogen and carbon monoxide is adjusted to a desired value. For example, a ratio $H_2/CO$ of hydrogen to carbon monoxide is adjusted to higher than 0/1 and 2/1 or lower.

As the reforming furnace 22, for example, a cylindrical member which can heat the mixed gas in the presence of water vapor at a temperature higher than a temperature for the thermal decomposition in the gasification furnace 20 can be adopted.

It is preferable that the pipe 41 be formed of a material which is inert with the mixed gas and, for example, be formed of a stainless steel pipe.

In the gas preparation device 10, the solid raw materials are thermally decomposed in the gasification furnace 20 to produce the mixed gas including hydrogen and carbon monoxide, and hydrocarbon in the mixed gas reacts with water in the reforming furnace 22 to be reformed into a mixed gas having a higher carbon monoxide concentration.

As in the case of the pipe 41, it is preferable that the pipe 42 be formed of a material which is inert with the mixed gas and, for example, be formed of a stainless steel pipe.

It is preferable that a gas purifier be provided in the pipe 42. By providing the gas purifier in the pipe 42, impurities in the mixed gas such as tar, sulfur, nitrogen, chlorine, or water can be removed.

As the gas purifier, for example, various well-known gas purifiers of the related art using a wet method, a dry method, or the like can be adopted. Examples of the wet method include a sodium hydroxide method, an ammonia absorption method, a lime-plaster method, and a magnesium hydroxide method. Examples of the dry method include an absorption method such as pressure swing absorption (PSA) and an electron beam method.

In the pipe 42, a cooler for reducing the temperature of the mixed gas may be provided. By providing the cooler in the pipe 42, it is easy to sufficiently reduce the temperature of the mixed gas supplied to the ethanol production device 12. In addition, by rapidly cooling the mixed gas using the cooler, the shift of equilibrium may be prevented, and the concentration of carbon monoxide can be maintained at a high level.

In the pipe 42, a gas disperser which saturates liquid such as water with the mixed gas by aeration or the like may be provided such that the liquid saturated with the mixed gas is supplied to the ethanol production device 12.

The ethanol production device 12 brings the mixed gas, which has been supplied from the gas preparation device 10, into contact with a first catalyst to obtain ethanol. In the ethanol production device 12 according to the embodiment, a microorganism capable of ethanol fermentation using carbon monoxide as a substrate is used as the first catalyst.

In the ethanol production device 12, by bringing the mixed gas into contact with the first catalyst, a primary product including ethanol is obtained.

The ethanol production device 12 is not particularly limited as long as it can produce ethanol by ethanol fermentation using a microorganism. For example, a well-known bioreactor can be adopted. Examples of the bioreactor include a continuously stirred tank reactor, an immobilized cell reactor, a trickle bed reactor, a bubble column, a gas lift fermenter, a membrane reactor (for example, a hollow fiber membrane reactor), and a static mixer.

As a material of the ethanol production device 12, a material which is inert with the mixed gas and ethanol is preferable.

As the microorganism used as the first catalyst, a well-known microorganism capable of ethanol fermentation in which carbon monoxide is used as a substrate can be adopted. For example, microorganisms described in Published Japanese Translation No. 2011-500100 of the PCT International Publication and Published Japanese Translation No. 2013-532481 of the PCT International Publication can be used. Specifically, for example, genus *Clostridium* (for example, *Clostridium ljungdahlii* or *Clostridium autoethanogenum*) can be used.

As the microorganism used as the first catalyst, one kind may be used alone, or two or more kinds may be used. The amount of the first catalyst used is not particularly limited and can be appropriately determined depending on the kind of the microorganism in a typical range in which the microorganism can be sufficiently cultured.

The microorganism capable of ethanol fermentation in which carbon monoxide is used as a substrate may be used in combination with a microorganism other than the above-described microorganism.

It is preferable that the pipe 43 be formed of a material which is inert with the primary product including ethanol and the like and, for example, be formed of a stainless steel pipe.

In the pipe 43, a pressure control portion which controls the internal pressure of the ethanol production device 12 may be provided. By the pressure control portion increasing the internal pressure of the ethanol production device 12 to be higher than the atmospheric pressure, the amount of hydrogen and carbon monoxide in the mixed gas which is dissolved in the liquid is increased, and the yield of ethanol is increased. The internal pressure of the ethanol production device 12 is controlled to be, for example, 0 to 1 MPa.

The purification device 14 removes materials (for example, by-products, water, unreacted mixed gas, a culture medium, or a catalyst) other than ethanol from the primary product. Examples of the purification device 14 include a distillation device, a gas-liquid separator, a solid-liquid separator, and a combination thereof.

The materials removed by the purification device 14 are exhausted through the exhaust pipe 44. It is preferable that the exhaust pipe 44 be formed of a material which is inert with the materials removed by the purification device 14 and, for example, be formed of a stainless steel pipe.

It is preferable that the pipe 45 be formed of a material which is inert with ethanol and, for example, be formed of a stainless steel pipe.

In the pipe 45, a heating device 28 which heats liquid ethanol to be gasified is provided. As a result, ethanol in the gasified state is supplied to the butadiene production device 16. For example, the heating device 28 heats ethanol to 90° C. to 150° C. to be gasified.

The heating device 28 is not particularly limited as long as it heats ethanol to be gasified. For example, a well-known heating device can be adopted. As a material of the heating device 28, a material which is inert with ethanol is preferable.

The butadiene production device 16 brings ethanol into contact with a second catalyst to obtain butadiene. The butadiene production device 16 includes: the reaction pipe 24 in which ethanol is brought into contact with a second catalyst to obtain butadiene; and the gas-liquid separator 26 that separates butadiene from a secondary product including butadiene and by-products (hydrogen, ethylene, and the like) obtained in the reaction pipe 24. The butadiene production device 16 may further include a well-known device, for example, a gas flow rate control portion that regulates the flow rate such as mass flow rate of gas.

The reaction pipe 24 is filled with the second catalyst to form a reactor bed 24a. It is preferable that the reaction pipe 24 be formed of a material which is inert with ethanol, butadiene, hydrogen, ethylene, and the like. In addition, it is preferable that the reaction pipe 24 have a shape that can endure heating at about 200° C. to 600° C. or pressing at about 10 MPa. As the reaction pipe 24, for example, a substantially circular stainless steel member is used.

The reactor bed 24a may be any one of a fixed bed, a moving bed, a fluidized bed, and the like.

The second catalyst is not particularly limited as long as butadiene can be synthesized from ethanol using it. As the second catalyst, for example, a catalyst including an oxide of a metal belonging to Group 4 to Group 13 in the periodic table and magnesium oxide is used. In the second catalyst, it is preferable that the metal belonging to Group 4 to Group 13 in the periodic table be bonded to magnesium oxide through one or more selected from magnesia and silica.

Preferable examples of the second catalyst include a catalyst in which tantalum oxide is bonded through magnesia and silica ($Ta_2O_5$/MgO/$SiO_2$ (mass ratio=2/83/15), refer to PCT International Publication No. WO2013/125389).

The second catalyst is produced using a well-known method.

Examples of a method of producing the second catalyst include a method including: dispersing a sol of a catalyst metal in a sol of one or more selected from magnesia and silica to obtain a catalyst sol; and firing the catalyst sol.

It is preferable that the pipe 46 and the pipe 47 be formed of a material which is inert with butadiene, hydrogen, ethylene, and the like and, for example, be formed of a stainless steel pipe.

In the embodiment, the pipe 46 includes a pressure control portion 30. The pressure control portion 30 is not particularly limited as long as it can adjust the internal pressure of the reaction pipe 24 to an arbitrary value. For example, a well-known pressure valve is used.

As the gas-liquid separator 26, a well-known gas-liquid separator formed of a material which is inert with butadiene, hydrogen, ethylene, and the like can be adopted.

In the gas-liquid separator 26, butadiene is separated by liquefying butadiene in a state where by-products including hydrogen, ethylene, and the like are gaseous. The separated and purified butadiene is collected in a storage tank or the like (not shown) through the pipe 47.

The return means 18 returns at least a portion of the gas other than butadiene from the butadiene production device 16 to the gas preparation device 10. The return means 18 includes a pipe through which the gas-liquid separator 26 of the butadiene production device 16 and the reforming furnace 22 of the gas preparation device 10 are connected.

It is preferable that the pipe of the return means 18 be formed of a material which is inert with hydrogen, ethylene, and the like and, for example, be formed of a stainless steel pipe.

Optionally, a valve, a pump, or the like is connected to the pipe of the return means 18.

In this example, the entire portion of the gas other than butadiene (including by-products such as hydrogen or ethylene) present in the gas phase of the gas-liquid separator 26 is returned to the reforming furnace 22. For example, a separation membrane may be provided in the pipe of the return means 18 such that hydrogen and ethylene are separated from the gas other than butadiene and then are returned.

A configuration of returning at least hydrogen in the gas other than butadiene is advantageous from the viewpoint that carbon dioxide, which is not used in the related art, can be used by converting it into carbon monoxide. A configuration of returning the entire portion of the gas other than butadiene is more advantageous from the viewpoint that the separation costs are not required and the viewpoint that the yield of ethanol can be further improved by reusing both hydrogen and hydrocarbon such as ethylene.

A position of the reforming furnace 22 to which the pipe of the return means 18 is connected is not particularly limited as long as carbon dioxide in the reforming furnace 22 is converted into carbon monoxide due to the equilibrium reaction and hydrocarbon is converted into carbon monoxide. For example, in a case where the reforming furnace 22 is a cylindrical member, the pipe of the return means 18 may be connected to a portion of the cylindrical body close to a gas supply port (close to the gasification furnace 20), to the center of the cylindrical body, or to a portion of the cylindrical body close to a gas exhaust port (close to the ethanol production device 12).

In the butadiene production system 1, the solid raw materials are thermally decomposed in the gasification furnace 20 of the gas preparation device 10 to produce the mixed gas including hydrogen and carbon monoxide. The mixed gas is supplied to the reforming furnace 22 through the pipe 41, and hydrocarbon in the mixed gas reacts with water in the reforming furnace 22 to be reformed into a mixed gas having a higher carbon monoxide concentration.

The reformed mixed gas is supplied from the reforming furnace 22 to the ethanol production device 12 through the pipe 42 and brought into contact with the first catalyst to react with the first catalyst such that a liquid primary product including ethanol is obtained. The primary product is supplied to the purification device 14 through the pipe 43 and is purified. The purified primary product which is gasified by the heating device 28 is supplied to the reaction pipe 24 of the butadiene production device 16 through the pipe 45.

Ethanol in the gaseous primary product supplied to the reaction pipe 24 is brought into contact with the second catalyst to react with the second catalyst such that a gaseous secondary product including butadiene, hydrogen, ethylene, and the like is obtained. The secondary product is supplied to the gas-liquid separator 26 through the pipe 46, and the liquid butadiene and the gas other than butadiene (including by-product such as hydrogen or ethylene) are separated from each other. Butadiene is collected through the pipe 47. The gas other than butadiene may include unreacted gas.

The gas other than butadiene including hydrogen, ethylene, and the like which are produced as by-products is returned to the reforming furnace 22 of the gas preparation device 10 by the return means 18. In the reforming furnace 22, carbon dioxide present around the periphery is converted into carbon monoxide using the returned hydrogen due to the equilibrium reaction represented by $CO_2 + H_2 \Leftrightarrow CO + H_2O$. In addition, carbon monoxide is synthesized from hydrocarbon such as ethylene due to the reaction represented by $C_nH_m + nH_2O \rightarrow nCO + (m/2+n)H_2$.

The butadiene production system 1 includes the return means 18. Therefore, carbon dioxide present in the gas preparation device 10 can be used for an ethanol production reaction by converting it into carbon monoxide using hydrogen which is produced by the butadiene production device 16 as a by-product. In addition, typically, hydrocarbon such as ethylene which is exhausted as carbon dioxide can be used for an ethanol production reaction by converting it into carbon monoxide due to an oxidation reaction. As a result, the amount of carbon dioxide exhausted can be reduced, and thus environmental load can be reduced.

In addition, in a configuration of returning at least hydrogen in the gas other than butadiene, carbon dioxide, which is not used in the related art, can be used as a raw material for an ethanol production reaction by converting it into carbon monoxide. Therefore, butadiene can be obtained with a higher yield as compared to a case where hydrogen is not returned.

(Butadiene Production Method)

Hereinafter, a method of producing the butadiene production system 1 will be described as an example of a butadiene production method according to the present invention. The butadiene production method according to the embodiment includes a gas preparation step, an ethanol production step, a butadiene production step, and a return step described below.

Gas preparation step: a step of heating raw materials to prepare a mixed gas including hydrogen and carbon monoxide Ethanol production step: a step of bringing the mixed gas into contact with a first catalyst to obtain ethanol Butadiene production step: a step of bringing the ethanol into contact with a second catalyst to obtain butadiene Return step: a step of returning at least a portion of the gas other than butadiene from the butadiene production step to the gas preparation step.

<Gas Preparation Step>

The gas preparation step according to the embodiment includes a gasification operation and a reforming operation, in the gasification operation, solid raw materials are thermally decomposed to produce the mixed gas including hydrogen and carbon monoxide, and in the reforming operation, hydrocarbon in the mixed gas is reformed into hydrogen and carbon monoxide by causing it to react with water.

In the gasification operation, in the gasification furnace 20 of the gas preparation device 10, a portion of the crushed solid raw materials such as biomass, organic waste (for example, waste plastic, waste paper, or waste cloth), or coal is fired in the presence of oxygen. As a result, the solid raw materials are thermally decomposed and gasified to produce the mixed gas including hydrogen and carbon monoxide.

A temperature for the thermal decomposition of the solid raw materials in the gasification operation is not particularly limited as long as it is a temperature at which the mixed gas including hydrogen and carbon monoxide is produced. The temperature for the thermal decomposition is preferably 200° C. to 1000° C. and more preferably 500° C. to 800° C. In a case where the temperature for the thermal decomposition is lower than the lower limit value, substantially no solid raw materials are gasified, and the object cannot be achieved. In a case where the temperature for the thermal decomposition is higher than the upper limit value, the proportion of the solid raw materials to be fired to increase the temperature increases, and the proportions of hydrogen and carbon monoxide in the mixed gas decrease.

In the reforming operation, in the reforming furnace 22, hydrocarbon in the mixed gas which is supplied from the gasification furnace 20 through the pipe 41 is caused to react with water. As a result, hydrocarbon is reformed into hydrogen and carbon monoxide, the concentration of carbon monoxide is increased, and thus a mixed gas having a desired ratio between hydrogen and carbon monoxide is obtained.

A temperature for heating the mixed gas in the reforming operation is higher than the temperature for the thermal decomposition in the gasification operation and is preferably 1000° C. to 2000° C. and more preferably 1000° C. to 1500° C. In a case where the heating temperature is the lower limit value or higher, the reaction sufficiently proceeds, and the concentration of carbon monoxide can be increased. In a case where the heating temperature is the upper limit value or lower, the material of the reforming furnace is not necessarily heat-resistant, and thus environmental load can be reduced.

The total proportion of hydrogen and carbon monoxide in the mixed gas prepared in the gas preparation step is preferably 50 vol % or higher, more preferably 80 vol % or higher, and still more preferably 90 vol % or higher. As the total proportion of hydrogen and carbon monoxide increases, the synthesis efficiency of ethanol can be easily increased. The upper limit value of the total proportion of hydrogen and carbon monoxide in the mixed gas is 100 vol %.

A volume ratio represented by hydrogen/carbon monoxide (hereinafter, also referred to as "the ratio $H_2/CO$") in the mixed gas prepared in the gas preparation step is preferably higher than 0/1 and 2/1 or lower, more preferably higher than 0/1 and 1/1 or lower, and still more preferably higher than 0/1 and 1/2 or lower. In a case where the ratio $H_2/CO$ is in the above-described range, the synthesis efficiency of ethanol can be easily increased.

The mixed gas may include not only hydrogen and carbon monoxide but also methane, ethane, ethylene, nitrogen, carbon dioxide, water, and the like.

<Ethanol Production Step>

The mixed gas whose temperature is decreased is supplied from the reforming furnace 22 of the gas preparation device 10 to the ethanol production device 12 through the pipe 42. In the ethanol production device 12, the microorganism as the first catalyst is present in a reaction solution including water, a culture medium, and the like, and an environment is adjusted so as to be capable of ethanol fermentation in which the microorganism is used. The mixed gas supplied to the ethanol production device 12 is brought into contact with the microorganism as the first catalyst such that the primary product including ethanol is obtained by ethanol fermentation.

In the embodiment, the primary product is a mixture of liquid (for example, ethanol or water) and gas (for example, unreacted mixed gas).

The temperature of the mixed gas supplied to the ethanol production device 12 is preferably decreased to 30° C. to 50° C. and is more preferably decreased to 35° C. to 40° C. In a case where the temperature of the mixed gas supplied is in the above-described range, a decrease in activity or extinction of the microorganism caused by heat is easily inhibited.

It is preferable that the supply amount of the mixed gas to the ethanol production device 12 be adjusted such that hydrogen and carbon monoxide are saturated in the liquid such as water. In a case where the supply amount of the mixed gas is as described above, ethanol can be produced more efficiently.

A reaction temperature in the ethanol production device 12 is preferably 30° C. to 45° C. and more preferably 35° C. to 40° C. In a case where the reaction temperature is in the above-described range, ethanol can be produced more efficiently.

An internal pressure (reaction pressure) of the ethanol production device 12 is preferably 0 to 1 MPa, more preferably 0.2 to 0.8 MPa, and still more preferably 0.4 to 0.6 MPa. In a case where the reaction pressure is the lower limit value or higher, hydrogen and carbon monoxide in the mixed gas are likely to be dissolved in the reaction solution, and ethanol can be produced more efficiently. In a case where the reaction pressure is the upper limit value or lower, high-pressure resistance is unnecessary, and environmental load can be reduced.

The primary product including ethanol obtained in the ethanol production device 12 is supplied to the purification device 14 through the pipe 43 and is purified by distillation, gas-liquid separation, and the like to remove materials other than ethanol. Next, the purified primary product which is heated to be gasified by the heating device 28 is supplied to the butadiene production device 16 through the pipe 45.

<Butadiene Production Step>

The primary product including ethanol is supplied to the reaction pipe 24 of the butadiene production device 16 and is brought into contact with the second catalyst of the reactor bed 24a. As a result, the secondary product including butadiene is obtained due to the reaction represented by the following formula (1). The secondary product according to the embodiment is gaseous.

$$2C_2H_5OH \rightarrow C_4H_6 + H_2 + 2H_2O \qquad (1)$$

The temperature (reaction temperature) at which the primary product is brought into contact with the second catalyst, that is, the temperature of the reactor bed 24a is preferably 300° C. to 500° C. and more preferably 350° C. to 450° C. In a case where the reaction temperature is the lower limit value or higher, the catalyst reaction speed is sufficiently increased, and butadiene can be produced more efficiently. In a case where the reaction temperature is the upper limit value or lower, deterioration in the second catalyst is likely to be inhibited.

The pressure (reaction pressure) at which the primary product is brought into contact with the second catalyst, that is, the internal pressure of the reaction pipe 24 is, for example, normal pressure to 1 MPa.

The proportion of ethanol in the primary product supplied in the butadiene production step is preferably 70 mass % or higher and more preferably 90 mass % or higher. In a case where the proportion of ethanol is the lower limit value or higher, the synthesis efficiency of butadiene can be further increased.

A space velocity of the primary product in the reactor bed 24a in terms of values measured under standard conditions is preferably 100 to 50000 UL-catalyst/hr, more preferably 200 to 10000 L/L-catalyst/hr, and still more preferably 300 to 5000 UL-catalyst/hr. The space velocity is appropriately adjusted in consideration of the reaction pressure, the reaction temperature, and the composition of the primary product.

Next, the secondary product is supplied from the reaction pipe 24 to the gas-liquid separator 26 through the pipe 46, the temperature is decreased, and the liquid butadiene and the gas other than butadiene (including by-product such as hydrogen or ethylene) are separated from each other. Butadiene is collected in a storage tank or the like (not shown) through the pipe 47.

<Return Step>

The gas other than butadiene (for example, hydrogen or ethylene) is returned from the butadiene production step to the reforming operation. Specifically, the gas other than butadiene (for example, hydrogen or ethylene) which is separated from butadiene by the gas-liquid separator 26 is returned to the reforming furnace 22 of the gas preparation device 10. By returning the gas other than butadiene to the reforming operation in a high-temperature environment, carbon dioxide present around the periphery in the reforming operation is converted into carbon monoxide using hydrogen in the gas due to the equilibrium reaction represented by $CO_2+H_2 \Leftrightarrow CO+H_2O$. In addition, carbon monoxide is synthesized from hydrocarbon such as ethylene due to the reaction represented by $C_nH_m+nH_2O \rightarrow nCO+(m/2+n)H_2$. As a result, the mixed gas which is rich in carbon monoxide is supplied to the ethanol production device 12.

In the return step, the entire portion of the gas other than butadiene (for example, hydrogen or ethylene) may be returned to the gas preparation step, or only hydrogen or ethylene which is separated from the gas other than butadiene may be returned to the gas preparation step. A configuration of returning at least hydrogen in the gas other than butadiene is advantageous from the viewpoint that carbon dioxide, which is not used in the related art, can be used by converting it into carbon monoxide. In addition, a configuration of returning the entire portion of the gas other than butadiene to the gas preparation step is more advantageous from the viewpoints of the costs and the yield of butadiene.

For example, in a case where hydrocarbon such as ethylene which may be included in the gas other than butadiene is returned together with hydrogen, the concentration of carbon monoxide in the mixed gas is further increased not only due to the equilibrium reaction using hydrogen but also due to the reaction represented by $C_nH_m+nH_2O \rightarrow nCO+(m/2+n)H_2$ using hydrocarbon such as ethylene. Therefore, the synthesis efficiency of ethanol is increased, and thus the yield of butadiene is increased. In addition, even in a case where hydrocarbon such as ethylene is returned, the hydrocarbon is converted into carbon monoxide and then is supplied to the ethanol production step. Therefore, an adverse effect of the hydrocarbon on the ethanol fermentation caused by the microorganism can be prevented.

In a case where hydrogen in the gas other than butadiene is returned, it is preferable that the amount of hydrogen returned be appropriately adjusted according to the amounts of carbon, hydrogen, and oxygen in the mixed gas. By adjusting the amount of hydrogen returned to control the equilibrium reaction, the amount of carbon dioxide is reduced, and environmental load can be easily reduced. In addition, butadiene can be easily produced with a high yield. In addition, instead of adjusting the amount of hydrogen returned, the amount of oxygen added in the gas preparation step may be adjusted.

In a case where the entire portion of the gas other than butadiene after gas-liquid separation is returned, it is preferable that the amount of the gas other than butadiene returned be determined after appropriately adjusting a ratio between hydrocarbon such as ethylene and water vapor in the mixed gas. By adjusting the amount of the gas other than butadiene returned to control the reaction, the amount of carbon dioxide is reduced, and environmental load can be easily reduced. In addition, butadiene can be easily produced with a high yield. In addition, instead of adjusting the amount of the gas other than butadiene returned, the amount of water vapor added in the gas preparation step may be adjusted.

As described above, in the butadiene production method according to the embodiment, the gas other than butadiene (for example, hydrogen or ethylene) is returned from the butadiene production step to the gas preparation step. As a result, carbon dioxide present around the periphery in the gas preparation step is converted into carbon monoxide using hydrogen included in the gas. In addition, hydrocarbon such as ethylene is caused to react with water vapor present around the periphery in the gas preparation step to produce carbon monoxide, and the produced carbon monoxide can be used in the ethanol production step. As a result, the amount of carbon dioxide exhausted including the amount of carbon dioxide produced from the by-products of the butadiene production step (for example, carbon dioxide produced by oxidation of hydrocarbon such as ethylene) can be reduced. Thus, environmental load can be reduced. In addition, by returning at least hydrogen in the gas other than butadiene, carbon dioxide, which is not used in the related art, can be used as a raw material for an ethanol production reaction by converting it into carbon monoxide. Therefore, butadiene can also be obtained with a higher yield as compared to a case where hydrogen is not returned.

In addition, in the embodiment, the microorganism, which is used as the first catalyst and performs ethanol fermentation in which carbon monoxide is used as a substrate, can use water in the reaction solution as a hydrogen source. As a result, in a configuration of using the microorganism as the first catalyst, even in a case where the gas other than butadiene is returned from the butadiene production step to the gas preparation step so as to increase the concentration of carbon monoxide in the mixed gas, the amount of hydrogen required for the ethanol fermentation is likely to be sufficient, and the synthesis efficiency of ethanol is particularly high.

Second Embodiment

Hereinafter, a second embodiment of the butadiene production system and the butadiene production method according to the present invention will be described. In the butadiene production system and the butadiene production method according to the embodiment, a metal catalyst is used as the first catalyst. Within a range where the effects of the present invention do not deteriorate, the metal catalyst may be used in combination with the microorganism capable of ethanol fermentation in which carbon monoxide is used as a substrate.

(Butadiene Production System)

Figure 2:
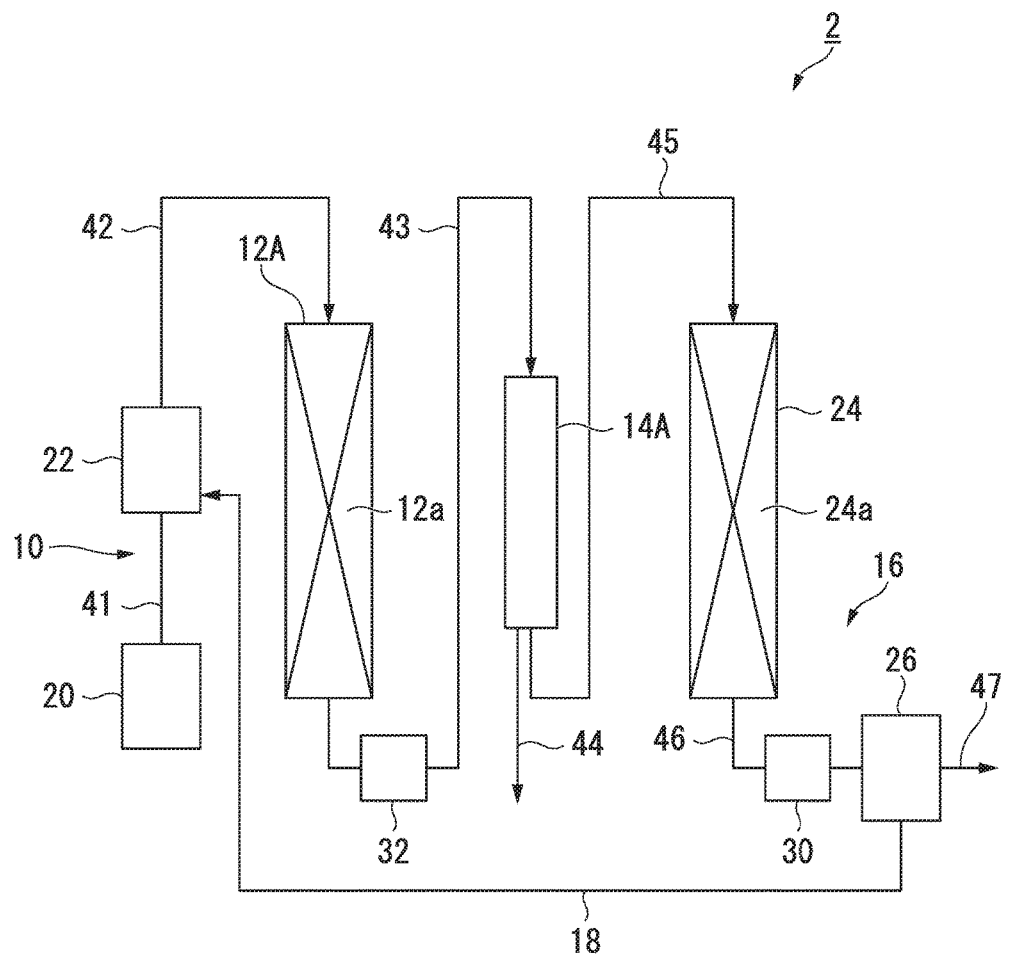
FIG. 2 is a schematic diagram showing another example of the butadiene production system according to the present invention.

FIG. 2 is a schematic diagram showing a butadiene production system 2 according to the embodiment. In FIG. 2, the same components as those in FIG. 1 will be represented by the same reference numerals, and the description thereof will not be repeated.

The butadiene production system 2 includes: the gas preparation device 10; an ethanol production device 12A that is provided downstream of the gas preparation device 10; a purification device 14A that is provided downstream of the ethanol production device 12A; a butadiene production device 16 that is provided downstream of the purification device 14A; and the return means 18 for returning at least a portion of the gas other than butadiene from the butadiene production device 16 to the gas preparation device 10.

The reforming furnace 22 and the ethanol production device 12A are connected to each other through the pipe 42. The ethanol production device 12A and the purification device 14A are connected to each other through the pipe 43. The exhaust pipe 44 is connected to the purification device 14A. The purification device 14A and the reaction pipe 24 of the butadiene production device 16 are connected to each other through the pipe 45.

The ethanol production device 12A is filled with the metal catalyst as the first catalyst to form a reactor bed 12a. It is preferable that the ethanol production device 12A be formed of a material which is inert with the mixed gas and ethanol. In addition, it is preferable that the ethanol production device 12A have a shape that can endure heating at about 100° C. to 500° C. or pressing at about 10 MPa. As the ethanol production device 12A, for example, a substantially circular stainless steel member is used.

The reactor bed 12a may be any one of a fixed bed, a moving bed, a fluidized bed, and the like.

The mixed gas is supplied to the ethanol production device 12A without any change from the gas state.

Examples of the catalyst metal used in the metal catalyst as the first catalyst include a hydrogenation-active metal and an aggregate of a hydrogenation-active metal and an auxiliary active metal described below.

In a case where ethanol is synthesized from a mixed gas of hydrogen and carbon monoxide using the metal catalyst, typically, a primary product including acetaldehyde or acetic acid is obtained in addition to ethanol due to the following reactions (2) to (6).

$$2H_2+2CO \rightarrow CH_3COOH \quad (2)$$

$$3H_2+2CO \rightarrow CH_3CHO+H_2O \quad (3)$$

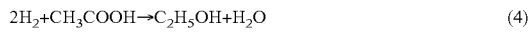
$$2H_2+CH_3COOH \rightarrow C_2H_5OH+H_2O \quad (4)$$

$$H_2+CH_3CHO \rightarrow C_2H_5OH \quad (5)$$

$$4H_2+2CO \rightarrow C_2H_5OH+H_2O \quad (6)$$

As the hydrogenation-active metal, a well-known metal of the related art in which ethanol can be synthesized from the mixed gas can be adopted. Examples of the hydrogenation-active metal include: alkali metals such as lithium and sodium; elements belonging to Group 7 in the periodic table, such as manganese and rhenium; elements belonging to Group 8 in the periodic table, such as ruthenium; elements belonging to Group 9 in the periodic table, such as cobalt and rhodium; and elements belonging to Group 10 in the periodic table, such as nickel and palladium.

Among these, hydrogenation-active metals, one kind may be used alone, and two or more kinds may be used in combination. As the hydrogenation-active metal, from the viewpoints further improving the CO conversion ratio and improving the selection ratio of ethanol, a combination of rhodium, manganese, and lithium, a combination of ruthenium, rhenium, and sodium, a combination of rhodium or ruthenium, an alkali metal, and another hydrogenation-active metal is preferable.

Examples of the auxiliary active metal include titanium, magnesium, and vanadium. By not only the hydrogenation-active metal but also the auxiliary active metal being supported on the metal catalyst, the CO conversion ratio, the selection ratio of ethanol and acetaldehyde can be further improved.

As the metal catalyst, a rhodium catalyst having a composition represented by the following Formula (m1) is preferable.

$$a\text{Rh}.b\text{Mn}.c\text{Me}^1.d\text{Me}^2 \quad (m1)$$

In Formula (m1), $Me^1$ represents an alkali metal, $Me^2$ represents an auxiliary active metal, and a, b, c, and d represent molar fractions in which a+b+c+d=1.

From the viewpoint of easily increasing the CO conversion ratio, a in Formula (m1) preferably represents 0.053 to 0.98, more preferably 0.24 to 0.8, and still more preferably 0.32 to 0.67.

From the viewpoint of easily increasing the CO conversion ratio, b in Formula (m1) preferably represents 0.0006 to 0.67, more preferably 0.033 to 0.57, and still more preferably 0.089 to 0.44.

From the viewpoint of easily increasing the CO conversion ratio, c in Formula (m1) preferably represents 0.00056 to 0.51, more preferably 0.026 to 0.42, and still more preferably 0.075 to 0.33.

d may be 0 (that is, the auxiliary active metal is not included) and may be more than 0 (that is, the auxiliary active metal is included). In a case where the auxiliary active metal is included, from the viewpoint of increasing the CO conversion ratio, d preferably represents 0.0026 to 0.94, more preferably 0.02 to 0.48, and still more preferably 0.039 to 0.25.

As the metal catalyst, a rhodium catalyst may be used in combination with a metal catalyst other than a rhodium catalyst.

As the metal catalyst, a so-called supported catalyst in which a catalyst metal is supported on a porous support is preferable. In the case of the supported catalyst, a ratio between ethanol and acetaldehyde in a product can be easily controlled.

A material of the porous support is not particularly limited, and examples thereof include silica, zirconia, titania, and magnesia. Among these, silica is preferable because various products thereof having different specific surface areas and different pore diameters are commercially available.

The supported catalyst can be produced using a well-known method of producing a supported catalyst of the related art. Examples of the method include an impregnation method and an ion exchange method. Among these, an impregnation method is preferable. In a case where the metal catalyst is produced using an impregnation method, a metal is more uniformly dispersed, and the contact efficiency between the metal catalyst and the mixed gas is further improved. Therefore, the CO conversion ratio and the selection ratio of ethanol and acetaldehyde can be further improved.

In the embodiment, the pipe 43 includes a pressure control portion 32. The pressure control portion 32 is not particularly limited as long as it can adjust the internal pressure of the ethanol production device 12A to an arbitrary value. For example, a well-known pressure valve is used.

The purification device 14A removes materials (for example, acetic acid, ethyl acetate, unreacted mixed gas, a culture medium, or a catalyst) other than ethanol and acetaldehyde from the primary product. By using the second catalyst in the butadiene production device 16, butadiene can be synthesized from ethanol and acetaldehyde.

Examples of the purification device 14A include a device including a separation membrane. Examples of the separation membrane include an acidic gas-containing gas treatment separation membrane described in PCT International Publication No. WO2014/080670 and a porous support-zeolite membrane composite described in PCT International Publication No. WO2013/125661.

In the butadiene production system 2, as in the case of the butadiene production system 1, the mixed gas is prepared in the gas preparation device 10.

The mixed gas is supplied from the reforming furnace 22 to the ethanol production device 12A through the pipe 42 and brought into contact with the first catalyst to react with the first catalyst such that a gaseous primary product including ethanol and acetaldehyde is obtained. The primary product is supplied to the purification device 14A through the pipe 43 and is purified. The reformed primary product is supplied to the butadiene production device 16 through the pipe 45.

In the butadiene production device 16, as in the case of the butadiene production system 1, a gaseous secondary product including butadiene, hydrogen, ethylene, and the like is obtained and the liquid butadiene and the gas other than butadiene (for example, hydrogen or ethylene) are separated from each other. Butadiene is collected through the pipe 47.

The gas other than butadiene (for example, hydrogen or ethylene) is returned to the reforming furnace 22 of the gas preparation device 10 by the return means 18. In the reforming furnace 22, carbon dioxide present around the periphery is converted into carbon monoxide using hydrogen in the returned gas other than butadiene due to the equilibrium reaction represented by $CO_2+H_2 \Leftrightarrow CO+H_2O$. In addition, the concentration of carbon monoxide in the mixed gas is further increased due to the reaction represented by $C_nH_m+nH_2O \rightarrow nCO+(m/2+n)H_2$ using hydrocarbon such as ethylene.

In the butadiene production system 2, as in the case of the butadiene production system 1, carbon dioxide present in the gas preparation device 10 can be used for an ethanol production reaction by converting it into carbon monoxide using hydrogen which is produced by the butadiene production device 16 as a by-product. In addition, hydrocarbon such as ethylene is caused to react with water vapor present in the gas preparation device 10 to produce carbon monoxide, and the produced carbon monoxide can be used in the ethanol production reaction. Therefore, environmental load can be reduced, and butadiene can be obtained with a higher yield as compared to a case where hydrogen, ethylene, and the like which are produced in the butadiene production device as by-products are not returned.

(Butadiene Production Method)

Hereinafter, a butadiene production method using the above-described butadiene production system 2 will be described. As in the case of the butadiene production system 1, the butadiene production method according to the embodiment includes a gas preparation step, an ethanol production step, a butadiene production step, and a return step described below.

<Gas Preparation Step>

The gas preparation step according to the embodiment is performed using the same method as in the butadiene production system 1.

A ratio $H_2/CO$ in the mixed gas prepared in the gas preparation step according to the embodiment is preferably 1/2 to 4/1, more preferably 1/1 to 3/1, and still more preferably 1.5/1 to 2.5 to 1. In a case where the ratio $H_2/CO$ is in the above-described range, the yield of ethanol can be easily increased.

The mixed gas may include not only hydrogen and carbon monoxide but also methane, ethane, ethylene, nitrogen, carbon dioxide, water, and the like.

<Ethanol Production Step>

The mixed gas is supplied from the reforming furnace 22 of the gas preparation device 10 to the ethanol production device 12A through the pipe 42. The mixed gas supplied to the ethanol production device 12 is brought into contact with the metal catalyst as the first catalyst such that the primary product including ethanol and acetaldehyde is obtained.

In the embodiment, the primary product is gaseous.

The temperature (reaction temperature) at which the mixed gas is brought into contact with the metal catalyst as the first catalyst, that is, the temperature of the reactor bed 12a is preferably 150° C. to 450° C., more preferably 200° C. to 400° C., and still more preferably 250° C. to 350° C. In a case where the reaction temperature is the lower limit value or higher, the catalyst reaction speed is sufficiently increased, and ethanol can be produced more efficiently. In a case where the reaction temperature is the upper limit value or lower, the selection ratio of ethanol can be increased.

The pressure (reaction pressure) at which the mixed gas is brought into contact with the metal catalyst as the first catalyst, that is, the internal pressure of the ethanol production device 12A is preferably 0.5 to 10 MPa, more preferably 1 to 7.5 MPa, and still more preferably 2 to 5 MPa. In a case where the reaction pressure is the lower limit value or higher, the catalyst reaction speed is sufficiently increased, and ethanol can be produced more efficiently. In a case where the reaction pressure is the upper limit value or lower, the selection ratio of ethanol can be increased.

A space velocity of the mixed gas in the reactor bed 12a (a value obtained by dividing the supply amount of gas per unit time by the amount of the catalyst (in terms of volume)) in terms of values measured under standard conditions is preferably 10 to 100000 L/L-catalyst/hr, more preferably 1000 to 50000 L/L-catalyst/hr, and still more preferably 3000 to 20000 L/L-catalyst/hr. The space velocity is appropriately adjusted in consideration of the reaction pressure, the reaction temperature, and the composition of the mixed gas as a raw material.

A molar ratio represented by ethanol/acetaldehyde (hereinafter, also referred to as "ratio EtOH/AcH") in the primary product according to the embodiment is preferably 1/5 to 5/1. In a case where the ratio EtOH/AcH is in the above-described range, the synthesis efficiency of butadiene can be further increased.

The ratio EtOH/AcH in the primary product can be easily adjusted by combining the composition of the metal catalyst, the average pore diameter of the support of the metal catalyst, the reaction temperature, the reaction pressure, and the like. For example, in a case where the reaction temperature is increased, the selection ratio of ethanol is increased, and the ratio EtOH/AcH is increased.

The primary product including ethanol obtained in the ethanol production device 12A is supplied to the purification device 14A through the pipe 43 and is purified to remove materials other than ethanol and acetaldehyde. Next, the purified primary product is supplied to the butadiene production device 16 through the pipe 45.

<Butadiene Production Step and Return Step>

The butadiene production step and the return step according to the embodiment are performed using the same method as in the butadiene production system 1.

In the butadiene production method according to the embodiment, as in the first embodiment, hydrogen, ethylene, and the like which are produced in the butadiene production step as by-products are returned. As a result, carbon dioxide present around the periphery in the gas preparation step is converted into carbon monoxide using hydrogen included in the gas. In addition, hydrocarbon such as ethylene is caused to react with water vapor present around the periphery in the gas preparation step to produce carbon monoxide, and the produced carbon monoxide can be used in the ethanol production step. Therefore, environmental load can be reduced, and butadiene can be obtained with a high yield.

As described above, in the butadiene production system and the butadiene production method according to the present invention, butadiene can be produced with a high yield, and environmental load can be reduced.

In the present invention, as the first catalyst, the microorganism capable of ethanol fermentation in which carbon monoxide is used as a substrate is more preferable than the metal catalyst. In the metal catalyst used as the first catalyst, the efficiency of the ethanol production reaction is high under conditions where the proportion of hydrogen is higher than that of carbon monoxide. On the other hand, in addition, in the embodiment, the microorganism which performs ethanol fermentation in which carbon monoxide is used as a substrate can use water in the reaction solution as a hydrogen source. Therefore, at least ethanol can be more efficiently synthesized from hydrogen in the mixed gas rather than from carbon monoxide. Thus, the configuration of using the microorganism as the first catalyst is particularly advantageous in the present invention in which the concentration of carbon monoxide in the mixed gas is increased using hydrogen which is produced as a by-product during the production of butadiene.

The butadiene production system according to the present invention is not limited to the above-described butadiene production system 1 or 2.

For example, in the butadiene production system according to the present invention, the gas other than butadiene (for example, hydrogen or ethylene) may be returned from the gas-liquid separator of the butadiene production device to the gasification furnace of the gas preparation device, or the gas other than butadiene may be returned to a pipe between the gasification furnace and the reforming furnace. Within a range where carbon monoxide can be produced from hydrogen and hydrocarbon such as ethylene in the returned gas other than butadiene, the gas other than butadiene may be returned to a portion of the pipe, which is provided downstream of the reforming furnace, where the temperature of the mixed gas emitted from the reforming furnace is sufficiently held to be high.

The gas preparation device included in the butadiene production system according to the present invention is not particularly limited as long as it can heat the raw materials to produce the mixed gas including hydrogen and carbon monoxide. For example, the gas preparation device may include only the reforming furnace without including the gasification furnace, in which raw material gases such as natural gas or waste gas emitted from a factory are heated and reformed in the reforming furnace so as to prepare the mixed gas including hydrogen and carbon monoxide. The gas preparation device may include a gasification-reforming furnace including both functions of the gasification furnace and the reforming furnace.

The return means included in the butadiene production system according to the present invention may be means for storing hydrogen or by-products including hydrogen obtained from the butadiene production device in a storage tank or the like and returning the stored hydrogen or by-products to the gas preparation device using various kinds of transport means such as transport using a vehicle. However, from the viewpoint of reducing energy loss, it is preferable that the return means be return means using a pipe.

The butadiene production method according to the present invention is not limited to the method using the above-described butadiene production system 1 or 2.

In the butadiene production method according to the present invention, the gas other than butadiene may be returned from the butadiene production step to the gasification operation. The gas preparation step may include only the reforming operation without including the gasification operation. In the gas preparation step, the gasification operation and the reforming operation may be performed at the same time.

Hereinafter, the present invention will be described in detail using Examples. However, the present invention is not limited to the following description.

[Component Analysis]

The amounts of butadiene, hydrogen, and ethylene in a secondary product obtained in each example were measured by gas chromatography.

Example 1

Butadiene was produced using the butadiene production system 1 shown in FIG. 1.

Specifically, 400 g/hr of a simulated waste simulating an industrial waste (combustible content: 76%, ash content: 9%, water content: 15%, amount of heat: 4000 kcal/kg) was gasified in the gasification furnace 20, and a water vapor reforming reaction was performed in the reforming furnace 22. As a result, 625 NL/hr of a mixed gas was obtained. 2 g/hr of hydrogen and 12 g/hr of ethylene, which were produced as by-products from the gas-liquid separator 26 of the butadiene production device 16, were returned to the reforming furnace 22.

The mixed gas was supplied to a reaction solution including an inorganic salt in the ethanol production device 12, and 113 g/hr of ethanol was obtained using a microorganism catalyst reaction. As the microorganism as the first catalyst, genus *Clostridium* was used. In the ethanol production device 12, the reaction temperature was 37° C., and the reaction pressure was 0.6 MPa.

The primary product including ethanol obtained in the ethanol production device 12 was purified by a distiller as the purification device 14, was gasified, and was supplied to the butadiene production device 16. As a result, the secondary product including butadiene was obtained. As the second catalyst, a tantalum catalyst was used. In the reaction pipe 24, the reaction temperature was 420° C. and the reaction pressure was 0.1 MPa, and the supply amount of the gasified primary product was 113 g/hr.

In the butadiene production device 16, 53 g/hr of butadiene, 2 g/hr of hydrogen, and 14 g/hr of ethylene were obtained. The yield of butadiene was 90%.

Comparative Example 1

Butadiene was produced using the same method as in Example 1, except that hydrogen and ethylene which were produced as by-products in the butadiene production device 16 were not returned to the reforming furnace 22. In the reforming furnace 22, 615 NL/hr of a mixed gas was obtained. In the ethanol production device 12, 100 g/hr of ethanol was obtained.

In the butadiene production device 16, 47 g/hr of butadiene, 2 g/hr of hydrogen, and 12 g/hr of ethylene were obtained. The yield of butadiene was 80%.

REFERENCE SIGNS LIST

1, 2: BUTADIENE PRODUCTION SYSTEM
10: GAS PREPARATION DEVICE
12, 12A: ETHANOL PRODUCTION DEVICE
14, 14A: PURIFICATION DEVICE
16: BUTADIENE PRODUCTION DEVICE
18: RETURN MEANS
20: GASIFICATION FURNACE
22: REFORMING FURNACE
24: REACTION PIPE
26: GAS-LIQUID SEPARATOR
41 to 43, 45 to 47: PIPE
44: EXHAUST PIPE

The invention claimed is:

1. A butadiene production system, comprising:
a gas preparation device that heats raw materials to prepare a mixed gas comprising hydrogen and carbon monoxide;
an ethanol production device that is provided downstream of the gas preparation device and brings the mixed gas into contact with a first catalyst to obtain ethanol;
a butadiene production device that is provided downstream of the ethanol production device and brings the ethanol into contact with a second catalyst to obtain butadiene;
a return means for returning a gas excluding the butadiene from the butadiene production device to the gas preparation device; and
carbon dioxide present in the gas preparation device is converted into carbon monoxide through an ethanol production reaction.

2. The butadiene production system according to claim 1,
wherein the return means comprises a pipe through which the butadiene production device and the gas preparation device are connected.

3. The butadiene production system according to claim 1,
wherein the gas preparation device comprises a gasification furnace and a reforming furnace,
the gasification furnace thermally decomposes solid raw materials to produce the mixed gas comprising hydrogen and carbon monoxide, and
the reforming furnace is provided downstream of the gasification furnace and reforms hydrocarbon in the mixed gas into hydrogen and carbon monoxide.

4. The butadiene production system according to claim 3,
wherein the return means is means for returning the gas excluding the butadiene to the reforming furnace.

5. A method of producing butadiene, comprising:
a gas preparation step of heating raw materials to prepare a mixed gas comprising hydrogen and carbon monoxide;
an ethanol production step of bringing the mixed gas into contact with a first catalyst to obtain ethanol;
a butadiene production step of bringing the ethanol into contact with a second catalyst to obtain butadiene;

a return step of returning a gas excluding the butadiene from the butadiene production step to the gas preparation step; and
an ethanol production step of converting carbon dioxide present in the gas preparation step into carbon monoxide.

6. The method according to claim 5,
wherein the gas preparation step comprises a gasification operation and a reforming operation,
in the gasification operation, solid raw materials are thermally decomposed to produce the mixed gas comprising hydrogen and carbon monoxide, and
in the reforming operation, hydrocarbon in the mixed gas is reformed into hydrogen and carbon monoxide.

7. The method according to claim 6,
wherein the return step returns the gas excluding the butadiene to the reforming operation.

8. The butadiene production system according to claim 2,
wherein the gas preparation device comprises a gasification furnace and a reforming furnace,
the gasification furnace thermally decomposes solid raw materials to produce the mixed gas comprising hydrogen and carbon monoxide, and
the reforming furnace is provided downstream of the gasification furnace and reforms hydrocarbon in the mixed gas into hydrogen and carbon monoxide.

9. The butadiene production system according to claim 8,
wherein the return means is means for returning the gas excluding the butadiene to the reforming furnace.

10. The butadiene production system according to claim 1,
wherein the return means is configured to return the gas excluding the butadiene and comprising a hydrogen by-product generated in the butadiene production device.

11. The butadiene production system according to claim 10,
wherein the return means comprises a pipe through which the butadiene production device and the gas preparation device are connected.

12. The butadiene production system according to claim 10,
wherein the gas preparation device comprises a gasification furnace and a reforming furnace,
the gasification furnace thermally decomposes solid raw materials to produce the mixed gas comprising hydrogen and carbon monoxide, and
the reforming furnace is provided downstream of the gasification furnace and reforms hydrocarbon in the mixed gas into hydrogen and carbon monoxide.

13. The butadiene production system according to claim 12,
wherein the return means is configured to return the gas excluding the butadiene and comprising the hydrogen by-product to the reforming furnace.

14. The method according to claim 5,
wherein the gas excluding the butadiene returned in the return step to the gas preparation step comprises a hydrogen by-product generated in the butadiene production step.

15. The method according to claim 14,
wherein the gas preparation step comprises a gasification operation and a reforming operation,
in the gasification operation, solid raw materials are thermally decomposed to produce the mixed gas comprising hydrogen and carbon monoxide, and in the reforming operation, hydrocarbon in the mixed gas is reformed into hydrogen and carbon monoxide.

16. The method according to claim 15, wherein the return step returns the gas excluding the butadiene and comprising the hydrogen by-product to the reforming operation.

17. The butadiene production system according to claim 11, wherein the gas preparation device comprises a gasification furnace and a reforming furnace, the gasification furnace thermally decomposes solid raw materials to produce the mixed gas comprising hydrogen and carbon monoxide, and the reforming furnace is provided downstream of the gasification furnace and reforms hydrocarbon in the mixed gas into hydrogen and carbon monoxide.

18. The butadiene production system according to claim 17, wherein the return means is means for returning the gas excluding the butadiene and comprising the hydrogen by-product to the reforming furnace.

* * * * *